US008497290B2

(12) United States Patent
Manchanda

(10) Patent No.: US 8,497,290 B2
(45) Date of Patent: Jul. 30, 2013

(54) THIOCOLCHICINE DERIVATIVES, METHOD OF MAKING AND METHODS OF USE THEREOF

(75) Inventor: Rajesh Manchanda, Sudbury, MA (US)

(73) Assignee: Takeda Pharmaceuticals U.S.A., Inc., Deerfield, IL (US)

( * ) Notice: Subject to any disclaimer, the term of this patent is extended or adjusted under 35 U.S.C. 154(b) by 355 days.

(21) Appl. No.: 12/788,634

(22) Filed: May 27, 2010

(65) Prior Publication Data
US 2010/0305165 A1   Dec. 2, 2010

Related U.S. Application Data

(60) Provisional application No. 61/181,450, filed on May 27, 2009.

(51) Int. Cl.
 *A01N 43/40* (2006.01)
 *A61K 31/44* (2006.01)
 *C07C 211/00* (2006.01)
 *C07C 69/76* (2006.01)

(52) U.S. Cl.
 USPC ........... 514/354; 564/427; 564/426; 560/107; 514/541

(58) Field of Classification Search
 USPC .................. 514/354, 541; 560/107; 564/426, 564/427
 See application file for complete search history.

(56) References Cited

U.S. PATENT DOCUMENTS

| | | | |
|---|---|---|---|
| 2,820,029 A | 1/1958 | Muller et al. | |
| 5,175,342 A | 12/1992 | Brossi | |
| 5,178,878 A | 1/1993 | Wehling et al. | |
| 5,777,136 A | 7/1998 | Bombardelli | |
| 5,973,204 A | 10/1999 | Bombardelli | |
| 6,150,140 A | 11/2000 | Bombardelli | |
| 6,221,392 B1 | 4/2001 | Khankari et al. | |
| 2003/0118642 A1 | 6/2003 | Norman et al. | |
| 2004/0204494 A1* | 10/2004 | Kim et al. ................ | 514/616 |
| 2007/0129315 A1 | 6/2007 | Bombardelli | |
| 2009/0011479 A1 | 1/2009 | Ponzone | |

FOREIGN PATENT DOCUMENTS
EP   0356137 A2   2/1990

OTHER PUBLICATIONS

West, Anthony R., Solid State Chemistry and its Applications, Wiley, New York, 1988, pp. 358 & 365.*
Bai et al., Mapping the Binding Site of Colchicinoids on β-Tubulin, 2-Chloroacetyl-2-Demethylthiocolchicine Covalently Reacts Predominantly with Cysteine 239 and Secondarily with Cysteine 354, Journal of Biological Chemistry, vol. 275, No. 51, pp. 40443-40452, 2000.
Boye et al., Synthesis of carbon-14 labeled electrophilic ligands of the colchicine binding site of tubulin: chloroacetates of demethylthiocolchicines and of N-acetylcolchinol; isothiocyanate of 9-deoxy-N-acetylcolchinol, Journal of Labelled Compounds and Radiopharmaceuticals (1993), 33(4), 293-99.
Gelmi et al., Novel 3-O-Glycosyl-3-demethylthiocolchicines as Ligands for Glycine and g-Aminobutyric Acid Receptors, Journal of Medicinal Chemistry (2007), 50(9), 2245-2248.
Kerekes et al., Esters of 1-O-dimethylthiocolchicines: formation of isomers in chloroform solution, Helvetica Chimica Acta (1985), 68(3), 571-80.
Muzaffar et al., Phenolic congeners of colchicine: preparation and characterization of phenolic and catecholic analogs of colchicine and thiocolchicine, Heterocyles (1989), 28(1), 365-72.
Nakagawa-Goto et al., Antitumor agents. Part 236: Synthesis of water-soluble colchicine derivatives, Bioorganic & Medicinal Chemistry Letters 15 (2005) 235-238.
Sharma et al. Selective Ether-cleavage of Thiocolchicoside and Thiocolchicine: Characterization of 3- and 2-Demethylthiocolchicone and Catecholic Congeners, Heterocycles, 1983, vol. 20, No. 8, p. 1587.
Shelkov et al., Selective esterifications of alcohols and phenols through carbodiimide couplings, Org. Biomol. Chem., (2004) vol. 2, 397-401.
Trellu et al., New metabolic and pharmacokinetic characteristics of thiocolchicoside and its active metabolite in healthy humans, Fundamental & Clinical Pharmacology, 18, (2004) 493-501.
STN CAS Registry No. 913524-65-9 (2010) 1 page.
STN CAS Registry No. 123417-78-7 (2010) 1 page.
STN CAS Registry No. 178492-27-8 (2010) 1 page.
STN CAS Registry No. 148731-66-2 (2010) 1 page.
STN CAS Registry No. 2730-86-1 (2010) 1 page.
STN CAS Registry No. 831197-69-4 (2010) 1 page.
STN CAS Registry No. 139889-39-7 (2010) 1 page.
STN CAS Registry No. 97043-00-0 (2010) 1 page.
STN CAS Registry No. 214281-96-6 (2010) 1 page.
STN CAS Registry No. 104158-08-9 (2010) 1 page.
STN CAS Registry No. 913524-48-8 (2010) 1 page.
STN CAS Registry No. 123417-77-6 (2010) 1 page.
STN CAS Registry No. 910620-97-2 (2010) 1 page.
STN CAS Registry No. 123643-50-5 (2010) 1 page.
STN CAS Registry No. 123643-55-0 (2010) 1 page.
STN CAS Registry No. 920743-19-7 (2010) 1 page.
International Search Report; International Application No. PCT/US2010/036325; International Filing Date May 27, 2010; 6 pages.
Written Opinion of the International Searching Authority; International Application No. PCT/US2010/036325; International Filing Date May 27, 2010; 6 pages.
WO0154674A1; Aug. 2, 2001; Abstract Only (1 page).
WO2007009772A1; Jan. 25, 2007; Abstract Only (2 pages).

* cited by examiner

Primary Examiner — Sreeni Padmanabhan
Assistant Examiner — Uma Ramachandran
(74) Attorney, Agent, or Firm — Cantor Colburn LLP

(57) ABSTRACT

Disclosed herein are thiocolchicine derivatives suitable for use as muscle relaxants, methods of making the derivatives, and compositions comprising the derivatives.

6 Claims, No Drawings

THIOCOLCHICINE DERIVATIVES, METHOD OF MAKING AND METHODS OF USE THEREOF

CROSS REFERENCE TO RELATED APPLICATION

This application claims the benefit of U.S. Provisional Application Ser. No. 61/181,450 filed May 27, 2009, which is hereby incorporated by reference in its entirety.

BACKGROUND

The thiocolchicine derivative thiocolchicoside (N-[(7S)-3-β-D-glucopyranosyloxy)-5,6,7,9-tetrahydro-1,2-dimethoxy-10-(methylthio)-9-oxobenzo[a]heptalen-7-yl]-acetamide also known as 3-demethylthiocolchicine glucoside; CAS Registry No. 602-41-5) is a known skeletal muscle relaxant. Studies have suggested that thiocolchicoside is metabolized in vivo into an aglycone derivative via deglycosylation and subsequent formation of a 3-O-glucuronidated aglycone derivative. See, Trellu et al., "New metabolic and pharmacokinetic characteristics of thiocolchicoside and its active metabolite in healthy humans", Fundamental & Clinical Pharmacology, 18, (2004) 493-501. The aglycone derivative exhibited no muscle relaxant activity in a rat model while the 3-O-glucuronidated aglycone derivative was found to exhibit muscle relaxant activity similar to that of thiocolchicoside. Id.

There remains a need in the art for new compounds exhibiting muscle relaxant activity similar to, or greater than, thiocolchicoside.

SUMMARY

In one embodiment, a compound according to structure (I)

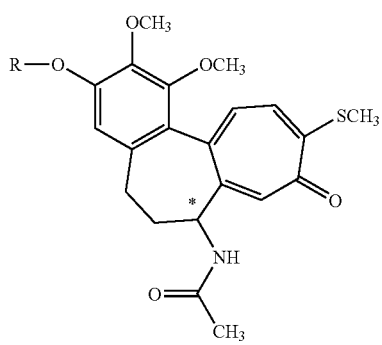

(I)

wherein R is a.) —C(=O)-(G)-C(=O)OR$^1$ where R$^1$ is hydrogen or $C_1$-$C_6$ alkyl and G is $C_1$-$C_6$ alkylene or $C_2$-$C_6$ alkenylene; b.) an amino acid derivative linked through the carboxylate group with the proviso that the amino acid is not glycine; c.) —CH$_2$—O(C=O)R$^2$ where R$^2$ is $C_1$-$C_6$ alkyl or $C_1$-$C_6$ alkoxy; d.) —C(=O)R$^3$, where R$^3$ is a heteroaryl or a substituted phenyl substituted with 1, 2, or 3 substituents independently chosen from hydroxy, amino, cyano, halogen, $C_1$-$C_6$alkyl, $C_3$-$C_7$cycloalkyl, $C_1$-$C_6$alkoxy, mono- and di-($C_1$-$C_4$alkyl)amino, —COOH, $C_2$-$C_6$alkoxycarbonyl, $C_1$-$C_6$haloalkyl, or $C_1$-$C_6$haloalkoxy; e.) —C(=O)-(G)-C(=O)R$^1$ where R$^1$ is hydrogen or $C_1$-$C_6$ alkyl and G is $C_1$-$C_6$ alkylene or $C_2$-$C_6$ alkenylene; f.) —C(=O)-(G)-SO$_3$R$^4$ where R$^4$ is hydrogen or $C_1$-$C_3$ alkyl and G is $C_1$-$C_6$ alkylene or $C_2$-$C_6$ alkenylene; g.) —C(=O)-(G)-N(R$^5$)$_2$ where each individual R$^5$ is hydrogen or $C_1$-$C_6$ alkyl and G is $C_1$-$C_6$ alkylene or $C_2$-$C_6$ alkenylene; or h.) —C(=O)O-(G)-OC(=O)R$^6$ where R$^6$ is hydrogen or $C_1$-$C_6$ alkyl and G is $C_1$-$C_6$ alkylene or $C_2$-$C_6$ alkenylene; or a pharmaceutically acceptable salt, solvate, hydrate, crystalline form, non-crystalline form, or stereoisomer thereof.

In another embodiment, a pharmaceutical composition comprises a compound according to structure (I) and a pharmaceutically acceptable excipient.

In yet another embodiment, a method of treating a patient in need thereof comprises administering to the patient a compound according to structure (I), or a composition comprising a compound according to structure (I) and a pharmaceutically acceptable excipient.

These and other embodiments, advantages and features of the present invention become clear when detailed description and examples are provided in subsequent sections.

DETAILED DESCRIPTION

Disclosed herein are thiocolchicine derivatives, compositions comprising the thiocolchicine derivatives, and uses thereof, particularly as a muscle relaxant. The thiocolchicine derivatives are suitable for use as a muscle relaxant while at the same time being non-sedating.

In one embodiment, a thiocolchicine derivative comprises a compound according to structure (I)

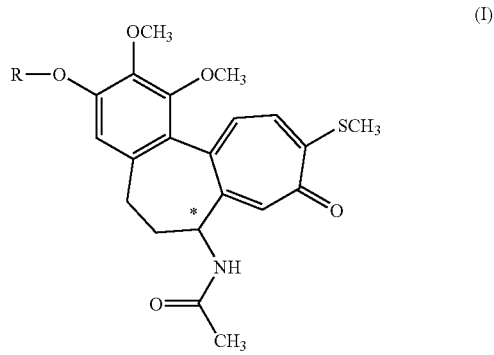

(I)

wherein R is
a.) —C(=O)-(G)-C(=O)OR$^1$ where R$^1$ is hydrogen or $C_1$-$C_6$ alkyl and G is $C_1$-$C_6$ alkylene or $C_2$-$C_6$ alkenylene, specifically —C(=O)(CH$_2$)$_x$C(=O)OR$^1$ where R$^1$ is hydrogen or $C_1$-$C_6$ alkyl, and x is 1, 2, 3, or 4;
b.) an amino acid derivative linked through the carboxylate group (e.g., valine)

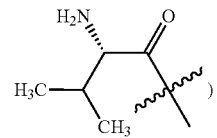

with the proviso that the amino acid is not glycine;
c.) —CH$_2$—O(C=O)R$^2$ where R$^2$ is $C_1$-$C_6$ alkyl or $C_1$-$C_6$ alkoxy;
d.) —C(=O)R$^3$, where R$^3$ is a heteroaryl or a substituted phenyl substituted with 1, 2, or 3 substituents independently chosen from hydroxy, amino, cyano, halogen, $C_1$-$C_6$alkyl, $C_3$-$C_7$cycloalkyl, $C_1$-$C_6$alkoxy, mono- and di-($C_1$-$C_4$alkyl)amino, —COOH, $C_2$-$C_6$alkoxycarbonyl, $C_1$-$C_6$haloalkyl, or $C_1$-$C_6$haloalkoxy;

e.) —C(=O)-(G)-C(=O)$R^1$ where $R^1$ is hydrogen or $C_1$-$C_6$ alkyl and G is $C_1$-$C_6$ alkylene or $C_2$-$C_6$ alkenylene, specifically —C(=O)($CH_2$)$_x$C(=O)$R^1$ where $R^1$ is hydrogen or $C_1$-$C_6$ alkyl, and x is 1, 2, 3, or 4;

f.) —C(=O)-(G)-$SO_3R^4$ where $R^4$ is hydrogen or $C_1$-$C_3$ alkyl and G is $C_1$-$C_6$ alkylene or $C_2$-$C_6$ alkenylene, specifically —C(=O)($CH_2$)$_x$$SO_3R^4$ where $R^4$ is hydrogen or $C_1$-$C_3$ alkyl and x is 1, 2, 3, or 4, compounds where $R^4$ is hydrogen may provide increased aqueous solubility for the thiocolchicine derivative;

g.) —C(=O)-(G)-N($R^5$)$_2$ where each individual $R^5$ is hydrogen or $C_1$-$C_6$ alkyl and G is $C_1$-$C_6$ alkylene or $C_2$-$C_6$ alkenylene, specifically —C(=O)($CH_2$)$_x$N($R^5$)$_2$ where each individual $R^5$ is $C_1$-$C_6$ alkyl and x is 1, 2, 3, or 4;

h.) —C(=O)O-(G)-OC(=O)$R^6$ where $R^6$ is hydrogen or $C_1$-$C_6$ alkyl and G is $C_1$-$C_6$ alkylene or $C_2$-$C_6$ alkenylene, specifically —C(=O)O($CH_2$)$_x$OC(=O)$R^6$ where $R^6$ is hydrogen or $C_1$-$C_6$ alkyl and where x is 1, 2, 3, or 4, this R group may provide increased aqueous solubility for the thiocolchicine derivative;

or a pharmaceutically acceptable salt, solvate, hydrate, crystalline form, non-crystalline form, or stereoisomer thereof.

The stereocenter of structure (I) indicated by "*" can be racemic, a mixture of R and S enriched in either the R or S isomer, in the R configuration, or in the S configuration. In one embodiment, the stereocenter of structure (I) indicated by "*" is in the S configuration.

Exemplary compounds of structure (I) wherein R is a.) —C(=O)-(G)-C(=O)$OR^1$ are when G is methylene, ethylene, ethenylene (—CH=CH—), or propylene, and $R^1$ is hydrogen, methyl, ethyl, n-propyl or isopropyl, specifically hydrogen. Compounds according to group a.) can be prepared by reacting 3-demethylthiocolchicine (CAS No. 87424-25-7) with a suitable acid anhydride (e.g., succinic anhydride, maleic anhydride, etc.), and optionally followed by esterification of the resulting carboxylic acid using procedures well known in the art. Alternative synthetic routes to achieve the derivatives where $R^1$ is $C_1$-$C_6$ alkyl is via a carbodiimide-mediated coupling of 3-demethylthiocolchicine and an appropriate carboxylic acid reagent using dicyclohexylcarbodiimide, diisopropylcarbodiimide, or ethyl-(N',N'-dimethylamino)propylcarbodiimide hydrochloride. See, Shelkov et al. "Selective esterifications of alcohols and phenols through carbodiimide couplings" Org. Biomol. Chem., 2004, 2, 397-401.

Exemplary compounds of structure (I) wherein R is b.) an amino acid linked through the carboxylate group include alanine, arginine, asparagine, aspartic acid, cysteine, glutamic acid, glutamine, histidine, isoleucine, leucine, lysine, methionine, phenylalanine, proline, pyrrolysine, serine, selenocysteine, threonine, tryptophan, tyrosine, valine, D, L, or D,L mixtures, and the like. Such compounds can be prepared by coupling 3-demethylthiocolchicine with a suitably N-protected amino acid followed by deprotection. The coupling reaction can be performed with a carbodiimide as previously discussed. Exemplary N-protected amino acids include fluorenylmethyloxycarbonyl (Fmoc)-valine, N-t-butoxycarbonyl valine, N-formyl valine, carbobenzyloxy (CBZ)-valine, and the like.

Exemplary compounds of structure (I) wherein R is c.) —$CH_2$—O(C=O)$R^2$ where $R^2$ is $C_1$-$C_6$ alkyl or $C_1$-$C_6$ alkoxy includes those where $R^2$ is methyl, ethyl, n-propyl, isopropyl, methoxy, ethoxy, n-propoxy, or isopropoxy. Such compounds can be prepared by reacting 3-demethylthiocolchicine with a base (e.g., $Na_2CO_3$) to form a phenoxide intermediate followed by a reaction with an appropriate alkyl halide or tosylate (e.g., chloromethyl acetate CAS No. 625-56-9, to form a compound where $R^2$ is methyl).

Exemplary compounds of structure (I) wherein R is d.) —C(=O)$R^3$ include compounds where $R^3$ is pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, or 5,6,7,8-tetrahydroisoquinoline. Other exemplary compounds include those where $R^3$ is phenyl substituted at the ortho, meta, or para position with methyl, ethyl, triflouromethyl, methoxy, ethoxy, triflouroethoxy, chloro, flouro, and the like. Such compounds can be prepared by reacting 3-demethylthiocolchicine with an appropriate acyl halide (e.g., 4-methylbenzoyl chloride, 2,4-dimethylbenzoyl chloride, or thiophene-2-carbonyl chloride) in the presence of a base (e.g., pyridine).

Exemplary compounds of structure (I) wherein R is e.) —C(=O)-(G)-C(=O)$R^1$ are when G is methylene, ethylene, ethenylene (—CH=CH—), or propylene, and $R^1$ is hydrogen, methyl, ethyl, n-propyl or isopropyl. Such compounds can be prepared using 3-demethylthiocolchicine, an appropriate carboxylic acid intermediate (e.g., 4-oxopentanoic acid CAS No. 123-76-2, 4-oxohexanoic acid CAS No. 1117-74-4, and 3-oxobutanoic acid CAS No. 541-50-4) and carbodiimide coupling procedures similar to those previously discussed for a.) —C(=O)-(G)-C(=O)$OR^1$ above.

Exemplary compounds of structure (I) wherein R is f.) —C(=O)-(G)-$SO_3R^4$ are when G is methylene, ethylene, ethenylene (—CH=CH—), or propylene, and $R^4$ is hydrogen, methyl, ethyl, n-propyl isopropyl, or a salt thereof, specifically hydrogen or a salt thereof. Such compounds can be prepared by reacting 3-demethylthiocolchicine with a haloalkanoic acid (e.g., 3-chloropropanoic acid CAS 107-94-8) followed by reacting the product with sulfite ion to form a salt of a sulfonic acid. The sulfonic acid can be converted to the sulfonic acid ester using methods well known in the art.

Exemplary compounds of structure (I) wherein R is g.) —C(=O)-(G)-N($R^5$)$_2$ where each individual $R^5$ is hydrogen or methyl, ethyl, n-propyl, or isopropyl, and G is methylene, ethylene, ethenylene (—CH=CH—), or propylene. Such compounds can be prepared using 3-demethylthiocolchicine, an appropriate carboxylic acid intermediate (e.g., 3-(dimethylamino)propanoic acid or 2-(dimethylamino)acetic acid) and carbodiimide coupling procedures similar to those previously discussed for a.) —C(=O)-(G)-C(=O)$OR^1$ above.

Exemplary compounds of structure (I) wherein R is h.) —C(=O)O-(G)-OC(=O)$R^6$ where G is methylene, ethylene, ethenylene (—CH=CH—), or propylene and $R^6$ is hydrogen, methyl, ethyl, n-propyl, or isopropyl. Such compounds can be prepared by reacting 3-demethylthiocolchicine with one equivalent of phosgene to form a haloformic ester, followed by subsequent reaction with an appropriate alcohol (e.g., 2-hydroxyethyl acetate, CAS No. 542-59-6 where G is ethylene and $R^6$ is methyl) to yield the desired product.

As used herein, "alkyl" includes straight chain, branched, and cyclic saturated aliphatic hydrocarbon groups, having the specified number of carbon atoms. Examples of alkyl include, but are not limited to, methyl, ethyl, n-propyl, isopropyl, n-butyl, 3-methylbutyl, t-butyl, n-pentyl, sec-pentyl, cyclopentyl, cyclohexyl, and n-hexyl. Specific alkyl groups include lower alkyl groups, those alkyl groups having 1, 2, 3, 4, 5, or 6 carbon atoms.

As used herein "haloalkyl" indicates straight chain, branched, and cyclic alkyl groups having the specified number of carbon atoms, substituted with 1 or more halogen atoms, generally up to the maximum allowable number of halogen atoms ("perhalogenated", e.g. perfluorinated). Examples of haloalkyl include, but are not limited to, trifluoromethyl, difluoromethyl, 2-fluoroethyl, and penta-fluoroethyl.

As used herein, "alkoxy" includes an alkyl group as defined above with the indicated number of carbon atoms attached through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Haloalkoxy" indicates a haloalkyl group as defined above attached through an oxygen bridge.

As used herein, the term "aryl" indicates aromatic groups containing only carbon in the aromatic ring or rings. Such aromatic groups may be further substituted with carbon or non-carbon atoms or groups. Typical aryl groups contain 1 or 2 separate, fused, or pendant rings and from 6 to about 12 ring atoms, without heteroatoms as ring members. Where indicated aryl groups may be substituted. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, anthracene, pentacene, fluorene, and bi-phenyl.

"Halo" or "halogen" as used herein refers to fluoro, chloro, bromo, or iodo.

Compounds are described using standard nomenclature. For example, any position not substituted by any indicated group is understood to have its valency filled by a bond as indicated, or a hydrogen atom.

"Heteroaryl" indicates a stable 5- to 7-membered monocyclic or 7- to 10-membered bicyclic heterocyclic ring which contains at least 1 aromatic ring that contains from 1 to 4, or specifically from 1 to 3, heteroatoms chosen from N, O, and S, with remaining ring atoms being carbon. When the total number of S and O atoms in the heteroaryl group exceeds 1, these hetero atoms are not adjacent to one another. In one embodiment, the total number of S and O atoms in the heteroaryl group is not more than 2. Examples of heteroaryl groups include pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, and 5,6,7,8-tetrahydroisoquinoline.

"Heterocycloalkyl" is used to indicate saturated cyclic groups containing from 1 to about 3 heteroatoms chosen from N, O, and S, with remaining ring atoms being carbon. Heterocycloalkyl groups have from 3 to about 8 ring atoms, and more typically have from 5 to 7 ring atoms. A $C_2$-$C_7$heterocycloalkyl group contains from 2 to about 7 carbon ring atoms and at least one ring atom chosen from N, O, and S. Examples of heterocycloalkyl groups include morpholinyl, piperazinyl, piperidinyl, and pyrrolidinyl groups.

"Alkoxycarbonyl" indicates an alkoxy group, as defined above, having the indicated number of carbon atoms, attached through a keto linkage. The carbon of the keto linker is not included in the numbering, thus a $C_2$alkoxycarbonyl has the formula $CH_3CH_2O(C=O)$—.

"Mono- or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

"Alkenyl" as used herein indicates hydrocarbon chains of either a straight or branched configuration comprising one or more unsaturated carbon-carbon bonds, which may occur in any stable point along the chain, such as ethenyl and propenyl.

"Substituted" as used herein means that any one or more hydrogens on the designated atom or group is replaced with a selection from the indicated group, provided that the designated atom's normal valence is not exceeded.

A dash ("—") that is not between two letters or symbols is used to indicate a point of attachment for a substituent. For example, —CHO is attached through carbon of the carbonyl group.

An "active agent" means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms (amorphous), and any polymorphs of the compound are contemplated herein. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

"Pharmaceutically acceptable salts" includes derivatives of an active agent, wherein the active agent is modified by making acid or base addition salts thereof, and further refers to pharmaceutically acceptable solvates, including hydrates, crystalline forms, non-crystalline forms, polymorphs, and stereoisomers of such salts. Examples of pharmaceutically acceptable salts include, but are not limited to, mineral or organic acid addition salts of basic residues such as amines; alkali or organic addition salts of acidic residues; and the like, or a combination comprising one or more of the foregoing salts. The pharmaceutically acceptable salts include salts and the quaternary ammonium salts of the active agent. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination comprising one or more of the foregoing salts.

The thiocolchicine derivatives of structure (I) can be formulated for oral, buccal, sublingual, mucosal, transdermal, rectal, vaginal, subcutaneous, intramuscular, and intravenous delivery. Depending upon the route of administration and the particular R group selected for the compounds of structure (I), the active species may be the thiocolchicine derivative itself, or a metabolite thereof. Not wishing to be bound by theory, it is expected that a potential active species is 3-O-glucuronidated 3-demethylthiocolchicine (e.g., (7S)-7-(acetylamino)-5,6,7,9-tetrahydro-1,2-dimethoxy-10-(methylthio)-9-oxobenzo[a]heptalen-3-yl β-D-glucopyranosiduronic acid, CAS No. 819802-34-1) derived from the cleavage of the R group of the thiocolchicine derivatives of structure (I) to form 3-demethylthiocolchicine followed by glucuronidation in vivo. Such a metabolite was shown with thiocolchicoside metabolism after oral administration. The R group may be cleaved in vivo via hydrolysis (e.g., in the acid environment in the stomach) or by enzymatic process from hydrolases, esterases, dehydrogenases, or oxidases. The choice of R group can be made to result in the formation of pharmaceutically acceptable side products of the leaving group when cleaved in vivo. Alternatively, if the thiocolchicine derivative is administered through a route other than via oral administration (e.g., transdermally, through the oral mucosa, intramuscularly, etc.) metabolism through mechanisms such as hydrolysis in the stomach or action by hydrolases present in the intestines can be avoided thereby preventing or substantially reducing the formation of the glucuronidated species.

By "oral dosage form" is meant to include a unit dosage form for oral administration that may be solid, semisolid, or liquid. An oral dosage form may optionally comprise a plurality of subunits such as, for example, microcapsules or microtablets. Multiple subunits may be packaged for administration in a single dose. Other exemplary dosage forms for oral administration include, for example, suspension, an emulsion, an orally disintegrating tablet including an effervescent tablet, a sublingual tablet, an orally dissolving strip, a gastro-resistant tablet, a soft capsule, a hard capsule, a gastro-resistant capsule, a tablet, a coated granule, a gastro-resistant granule, and the like.

By "subunit" is meant to include a composition, mixture, particle, pellet, etc., that can provide an oral dosage form alone or when combined with other subunits.

Solid dosage forms for oral administration include, but are not limited to, capsules, tablets, powders, and granules. In such solid dosage forms, the active agent may be admixed with one or more of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alignates, gelatin, polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate, or a combination comprising one or more of the foregoing additives. For capsules and tablets, the dosage forms may also comprise buffering agents.

Another suitable oral dosage form is a non-chewable, orally disintegrating tablet. These dosage forms can be made by methods known to those of ordinary skill in the art of pharmaceutical formulations. For example, Cima Labs has produced oral dosage forms including microparticles and effervescents, which rapidly disintegrate in the mouth and provide adequate taste-masking. Cima Labs has also produced a rapidly dissolving dosage form containing the active agent and a matrix that includes a nondirect compression filler and a lubricant. U.S. Pat. Nos. 5,178,878 and 6,221,392 provide teachings regarding orally disintegrating tablets.

An exemplary orally disintegrating tablet includes a mixture incorporating a water or saliva activated effervescent disintegration agent and subunits such as coated particles, specifically of a size such that chewing does not damage the structure of the subunit. The mixture including the subunits and effervescent disintegration agent may be formulated as a tablet of a size and shape adapted for direct oral administration to a patient. The tablet is substantially completely disintegrable upon exposure to water or saliva. The effervescent disintegration agent is present in an amount effective to aid in disintegration of the tablet, and to provide a distinct sensation of effervescence when the tablet is placed in the mouth of a patient.

The effervescent sensation is not only pleasant to the patient but also tends to stimulate saliva production, thereby providing additional water to aid in further effervescent action. Thus, once the tablet is placed in the patient's mouth, it will disintegrate rapidly and substantially completely without any voluntary action by the patient. Even if the patient does not chew the tablet, disintegration will proceed rapidly. Upon disintegration of the tablet, the subunits are released and can be swallowed as a slurry or suspension. The subunits thus may be transferred to the patient's stomach for dissolution in the digestive tract and systemic distribution of the active agent.

The term effervescent disintegration agent includes compounds which evolve gas. The preferred effervescent disintegration agents evolve gas by means of chemical reactions which take place upon exposure of the effervescent disintegration agent to water or to saliva in the mouth. The bubble or gas generating reaction is most often the result of the reaction of a soluble acid source and an alkali metal carbonate or carbonate source. The reaction of these two general classes of compounds produces carbon dioxide gas upon contact with water included in saliva.

Such water activated materials may be kept in a generally anhydrous state with little or no absorbed moisture or in a stable hydrated form since exposure to water will prematurely disintegrate the tablet. The acid sources or acid may be those which are safe for human consumption and may generally include food acids, acid anhydrides and acid salts. Food acids include citric acid, tartaric acid, malic acid, fumaric acid, adipic acid, and succinic acids etc. Because these acids are directly ingested, their overall solubility in water is less important than it would be if the effervescent tablet formulations were intended to be dissolved in a glass of water. Acid anhydrides and acid of the above described acids may also be used. Acid salts may include sodium, dihydrogen phosphate, disodium dihydrogen pyrophosphate, acid citrate salts and sodium acid sulfite.

Carbonate sources include dry solid carbonate and bicarbonate salts such as sodium bicarbonate, sodium carbonate, potassium bicarbonate and potassium carbonate, magnesium carbonate and sodium sesquicarbonate, sodium glycine carbonate, L-lysine carbonate, arginine carbonate, amorphous calcium carbonate, or a combination comprising at least one of the foregoing carbonates.

The effervescent disintegration agent is not always based upon a reaction which forms carbon dioxide. Reactants which evolve oxygen or other gasses which are safe are also considered within the scope. Where the effervescent agent includes two mutually reactive components, such as an acid source and a carbonate source, it is preferred that both components react substantially completely. Therefore, an equivalent ratio of components which provides for equal equivalents is preferred. For example, if the acid used is diprotic, then either twice the amount of a mono-reactive carbonate base, or an equal amount of a di-reactive base should be used for complete neutralization to be realized. However, the amount of either acid or carbonate source may exceed the amount of the other component. This may be useful to enhance taste or performance of a tablet containing an overage of either component. In this case, it is acceptable that the additional amount of either component may remain unreacted.

In general, the amount of effervescent disintegration agent useful for the formation of tablets is about 5 wt % to about 50 wt % based on the total weight of the final dosage form, specifically about 15 wt % and about 30 wt %, and more specifically about 20 wt % to about 25 wt %.

Other types of orally disintegrating tablets can be prepared without an effervescent agent by using a spray dried carbohydrate or sugar alcohol excipients (e.g. sorbitol, mannitol, xylitol, or a combination comprising at least one of the foregoing, and the like), optionally combined with a disintegrant (e.g. the disintegrant is selected from crospovidone, croscarmellose, sodium starch glycolate, pregelatinized starch, partially pregelatinized starch, or a combination comprising at least one of the foregoing, and the like), or a glidant (e.g. colloidal silica, silica gel, precipitated silica, or a combination comprising at least one of the foregoing, and the like). Suitable orally disintegrating tablets can be found in U.S. Patent Application Publication US20030118642 A1 to Norman et al. incorporated herein in its entirety.

Orally disintegrating tablets can be manufactured by well-known tableting procedures. In common tableting processes, the material which is to be tableted is deposited into a cavity, and one or more punch members are then advanced into the cavity and brought into intimate contact with the material to be pressed, whereupon compressive force is applied. The material is thus forced into conformity with the shape of the punches and the cavity.

The orally disintegrating tablets typically rapidly disintegrate when orally administered. By "rapid", it is understood that the tablets disintegrate in the mouth of a patient in less than about 7 minutes, and specifically between about 30 seconds and about 5 minutes, specifically the tablet should dissolve in the mouth between about 45 seconds and about 2 minutes. Disintegration time in the mouth can be measured by observing the disintegration time of the tablet in water at about 37° C. The tablet is immersed in the water without forcible agitation. The disintegration time is the time from immersion for substantially complete dispersion of the tablet as determined by visual observation. As used herein, the term "complete disintegration" of the tablet does not require dissolution or disintegration of the subunits or other discrete inclusions. In one embodiment, disintegration can be determined by USP 32 (Test <701>).

In another embodiment, the orally disintegrating tablets include those having a dissolution rate of more than 65% release of active agent within 15 minutes. A dissolution profile is a plot of the cumulative amount of active agent released as a function of time. A dissolution profile can be measured, for example, utilizing the standard test for dissolution according to USP 32 (Test <711>) or Drug Release Test <724>. A profile is characterized by the test conditions selected such as, for example, apparatus type, shaft speed, temperature, volume, and pH of the dissolution medium. More than one dissolution profile may be measured. For example, a first dissolution profile can be measured at a pH level approximating that of the stomach, and a second dissolution profile can be measured at a pH level approximating that of one point in the intestine or several pH levels approximating multiple points in the intestine.

A highly acidic pH may be employed to simulate the stomach and a less acidic to basic pH may be employed to simulate the intestine. By the term "highly acidic pH" is meant a pH of about 1 to about 4. A pH of about 1.2, for example, can be used to simulate the pH of the stomach. By the term "less acidic to basic pH" is meant a pH of greater than about 4 to about 7.5, specifically about 6 to about 7.5. A pH of about 6 to about 7.5, specifically about 6.8, can be used to simulate the pH of the intestine.

In another embodiment, the thiocochicine derivatives are formulated into an orally dissolving strip, which rapidly dissolves in the mouth to release the active agent within the strip. The orally dissolving strips generally comprise a water soluble polymer and a thiocolchicine derivative. Exemplary classes of water soluble polymers include water soluble cellulosic polymers, water soluble synthetic polymers, water soluble natural gums and polymers or derivatives thereof, or a combination comprising at least one of the foregoing. Exemplary water soluble cellulosic polymers include hydroxypropyl cellulose, hydroxypropylmethyl cellulose, hydroxyethyl cellulose, carboxymethyl cellulose, or a combination comprising at least one of the foregoing. Exemplary water soluble natural gums and polymers include amylose, dextran, casein, pullulan, gelatin, pectin, agar, carrageenan, xanthan gum, tragacanth, guar gum, acacia gum, arabic gum, sodium alginate, zein, or a combination comprising at least one of the foregoing. Exemplary water soluble synthetic polymers include polyethylene glycol, polyethylene oxide, polyvinyl pyrrolidone, polyvinyl alcohol, carboxyvinyl polymers, water soluble polyacrylic acid/acrylate, or a combination comprising at least one of the foregoing.

The water soluble polymer may be present in amounts of about 20 to about 95, specifically about 30 to about 85, and more specifically about 40 to about 75 wt % based on the total weight of the orally dissolving strip.

The orally dissolving strip can further optionally comprise a plasticizer in addition to the water soluble polymer and active agent. Exemplary plasticizers include propylene glycol, glycerin, glycerol, monoacetin, diacetin, triacetin, dimethyl phthalate, diethyl phthalate, dibutyl phthalate, dibutyl sebacate, triethyl titrate, tributyl citrate, triethyl citrate, triethyl acetyl citrate, castor oil, acetylated monoglycerides, sorbitol, or a combination comprising at least one of the foregoing. The plasticizer may be present in amounts of about 0 to about 20, specifically about 1 to about 15, and more specifically about 5 to about 10 wt % based on the total weight of the orally dissolving strip.

The orally dissolving strip can further optionally comprise an emulsifying agent in addition to the water soluble polymer and active agent. Exemplary emulsifying agents include polyvinyl alcohol, a sorbitan esters, a cyclodextrin, benzyl benzoate, glyceryl monostearate, a polyoxyethylene alkyl ether, a polyoxyethylene stearate, poloxamer, a polyoxyethylene castor oil derivative, a hydrogenated vegetable oil, a polysorbate, or a combination comprising at least one of the foregoing The emulsifying agent may be present in amounts of about 0 to about 20, specifically about 1 to about 15, and more specifically about 5 to about 10 wt % based on the total weight of the orally dissolving strip.

The orally dissolving strip can further optionally comprise a flavor or sweetener in addition to the water soluble polymer and active agent. Exemplary sweeteners include sugar, a monosaccharide, an oligosaccharide, aldose, ketose, dextrose, maltose, lactose, glucose, fructose, sucrose, a sugar polyol (e.g., mannitol, xylitol, sorbitol, erythritol, and the like), artificial sweeteners (e.g., acesulfame potassium, sucralose, aspartame, saccharin, sodium saccharin, and the like) or a combination comprising at least one of the foregoing. The sweetener may be present in amounts of about 0 to about 20, specifically about 1 to about 15, and more specifically about 5 to about 10 wt % based on the total weight of the orally dissolving strip.

In some embodiments, the orally dissolving formulations of the present invention may comprise an excipient. Suitable excipients include, but are not limited to, microcrystalline cellulose, colloidal silicon dioxide, talc, starch, or a combination comprising at least one of the foregoing. In some embodiments, the excipient may include talc as anti-adhering agent.

Other optional components that can be used to prepare the orally dissolving strip include a filler/diluent, a surfactant, a disintegrating agent, an antifoaming agent, an antioxidant, a buffering agent, a color, or a combination comprising at least one of the foregoing.

In one embodiment, particles of the thiocolchicine derivative are coated with a taste-masking polymer for greater patient acceptability. Exemplary taste-making polymers include meth/acrylic and meth/acrylate polymers and copolymers such as Eudragit® polymers from Evonik Industries (amino methacrylate copolymer, Eudragit® E PO, E 100, and E 12,5; and methacrylic acid copolymer Type A, B, and C, Eudragit® L 100, S 100, and L 100-55). Other taste-masking polymers include cellulose acetate phthalate, ethyl vinyl phthalate, polyvinyl acetate phthalate, a hydroxy alkyl cellulose phthalate, or a combination comprising at least one of the foregoing.

The taste-masking polymer can be used in an amount of about 1 to about 35 wt % based on the total weight of active agent and taste-masking polymer, specifically about 3 to about 20 wt %, and more specifically about 5 to about 10 wt %.

In one embodiment, the orally dissolving strip exhibits a drug loading of not more than 50% w/w of the film. Exemplary orally dissolving strips will comprise about 0.01 to about 50 mg of active agent per strip. In another embodiment, the orally dissolving strip has a thickness of about 0.1 to about 5.0 millimeters, specifically about 0.3 to about 4.0 and yet more specifically about 0.5 to about 2.5. In another embodiment the orally dissolving strip has a surface area of about 1.0 to about 6.0, specifically about 1.2 to about 4.0 and yet more specifically about 1.5 to about 2.0 square centimeters.

The orally dissolving strip once placed in the oral cavity may dissolve after less than about 60 seconds, specifically less than 30 seconds, and yet more specifically less than about 20 seconds.

A solvent can be used in the process to prepare the orally dissolving strip, including water, ethanol, 1-butanol, 2-butanol, 2-ethoxyethanol, ethyl acetate, methyl acetate, 3-methyl-1-butanol, methylethyl ketone, 2-methyl-1-propanol, isobutyl acetate, isopropyl acetate ethyl ether, tert-butylmethyl ether acetone, or a combination comprising at least one of the foregoing. The solvent is used for processing and then removed to result in the final product.

Methods of preparing orally dissolving strips involve solvent casting and film coating. The active agent is mixed with film-forming excipients and solvents such as water, ethanol, and the like. A thin coating of the mixture is cast on a moving, inert substrate and the coated substrate is moved through a drying oven to evaporate the solvent before die-cutting the dried film into strips. Another method involves hot-melt extrusion, by melting an active agent and excipient polymer blend which is then extruded through a die under molten conditions. The thin film is then cooled to room temperature and die-cut into strips.

The thiocolchicine derivatives disclosed herein are suitable for treating a patient in need thereof, specifically for use as a non-sedating muscle relaxant. The thiocolchicine derivatives can also be used as an anti-inflammatory or an anti-gout agent. The thiocolchicine derivative is administered in an amount sufficient to provide muscle relaxant activity to the patient. Amounts can be determined by the skilled artisan using techniques known in the art. Exemplary amounts of thiocolchicine derivatives can be about 0.01 to about 50 mg per day, specifically about 1 to about 40 mg per day, more specifically about 4 to about 30 mg per day, and yet more specifically about 8 to about 20 mg per day.

The following examples further illustrate the invention but, of course, should not be construed as in any way limiting its scope.

EXAMPLES

Preparation of 3-demethylthiocolchicine (CAS No. 87424-25-7)

3-Demethylthiocolchicine can be prepared from 3-demethylcolchicine by the reaction with sodium or potassium methylthiolate in water at temperatures between 0 to 30° C., specifically room temperature. 3-Demethylcolchicine can be obtained from plant species *Colchicum autumnale*. Alternatively, 3-demethylthiocolchicine can be prepared from the hydrolysis of thiocolchicoside with 80% phosphoric acid. Sharma et al. Heterocycles, 1983, Vol. 20, p. 1587. 3-Demethylthiocolchicine can be prepared from the procedure of Example 1 of U.S. Pat. No. 5,175,342, the specific example incorporated by reference herein.

Example 1

3-[4-Oxobutanoic acid]-3-demethylthiocolchicine

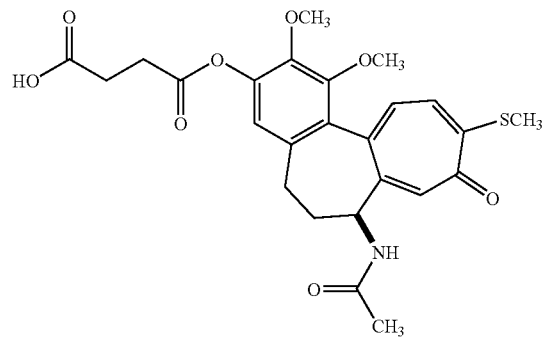 [SMILES: COc1c(OC(=O)CCC(=O)O)cc2c(c1OC)-c1ccc(SC)c(=O)cc1[C@@H](NC(C)=O)CC2]

3-Demethylthiocolchicine (100 mg) is dissolved in methylene chloride (3 ml) and triethylamine (0.5 ml) is added with succinic anhydride (5 equivalents) dissolved in 1 ml methylene chloride. The reaction is allowed to stir at room temperature for twelve hours, diluted with 15 ml methylene chloride and washed with 2N HCl, then brine. The organic layer is dried over Na$_2$SO$_4$ or MgSO$_4$, filtered to remove the drying agent, and stripped of solvent to yield 3-[4-oxobutanoic acid]-3-demethylthiocolchicine.

Example 2

3-[(Z)-4-Oxo-but-2-enoic acid]-3-demethylthiocolchicine

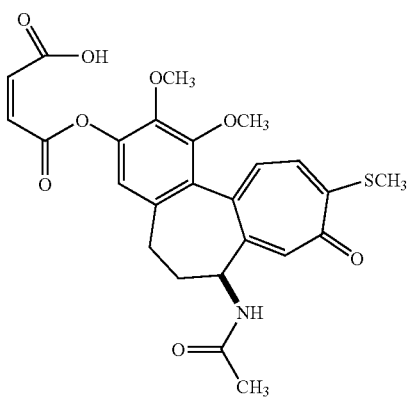 [SMILES: COc1c(OC(=O)/C=C\C(=O)O)cc2c(c1OC)-c1ccc(SC)c(=O)cc1[C@@H](NC(C)=O)CC2]

3-Demethylthiocolchicine (100 mg) is dissolved in methylene chloride (3 ml) and triethylamine (0.5 ml) is added with maleic anhydride (5 equivalents) dissolved in 1 ml methylene chloride. The reaction is allowed to stir at room temperature for twelve hours, diluted with 15 ml methylene chloride and washed with 2N HCl, then brine. The organic layer is dried over Na$_2$SO$_4$ or MgSO$_4$, filtered to remove the drying agent, and stripped of solvent to yield 3-[(Z)-4-oxo-but-2-enoic acid]-3-demethylthiocolchicine.

Example 3

3-[ethyl 4-oxobutanoate]-3-demethylthiocolchicine

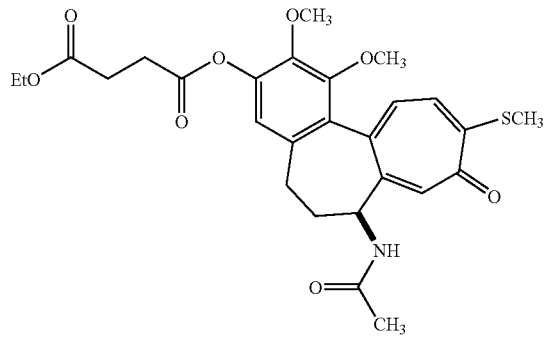 [SMILES: CCOC(=O)CCC(=O)Oc1cc2c(c(OC)c1OC)-c1ccc(SC)c(=O)cc1[C@@H](NC(C)=O)CC2]

3-Demethylthiocolchicine (1 mmol) and 4-ethoxy-4-oxobutanoic acid (CAS No. 1070-34-4, 1 mmol) is dissolved in acetonitrile (5 ml), optionally in the presence of 4-(N,N-dimethylamino)pyridine (DMAP, 0.15 equivalents). A solution of dicyclohexylcarbodiimide (1 mmol) in 1 ml acetonitrile is added to the reaction mixture and allowed to stir for 12 hours. The reaction mixture is filtered, stripped of acetonitrile and the resulting material is purified by flash chromatography on silica to yield the product 3-[ethyl 4-oxobutanoate]-3-demethylthiocolchicine.

Example 4

3-[methyl 4-oxobutanoate]-3-demethylthiocolchicine

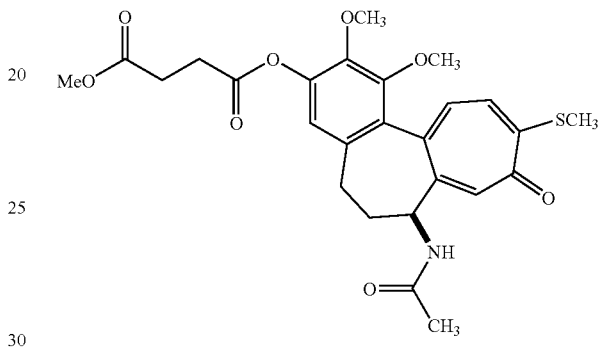

3-[methyl 4-oxobutanoate]-3-demethylthiocolchicine can be prepared in a similar process as in Example 3 using 4-methoxy-4-oxobutanoic acid CAS No. 3878-55-5.

Example 5

3-[Thiophene-2-carbonyl]-3-demethylthiocolchicine

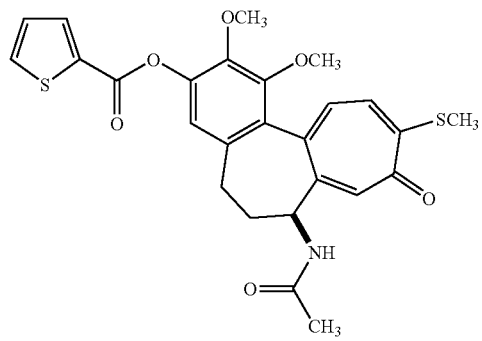 [SMILES: COc1c(OC(=O)c2cccs2)cc2c(c1OC)-c1ccc(SC)c(=O)cc1[C@@H](NC(C)=O)CC2]

3-Demethylthiocolchicine (100 mg) is dissolved in pyridine (3 ml) and cooled in an ice bath. A solution of thiophene-2-carbonyl chloride (CAS No. 5271-67-0, 1 equivalent) in 1 ml pyridine is added and the reaction is stirred for 5 hours. The reaction mixture is quenched with water, adjusted to pH 5 by the addition of 2N HCl, and methylene chloride. The solvent is stripped and the resulting material is purified by flash chromatography on silica to yield the product 3-[thiophene-2-carbonyl]-3-demethylthiocolchicine.

Example 6

3-[2,4-Dimethylbenzoyl]-3-demethylthiocolchicine

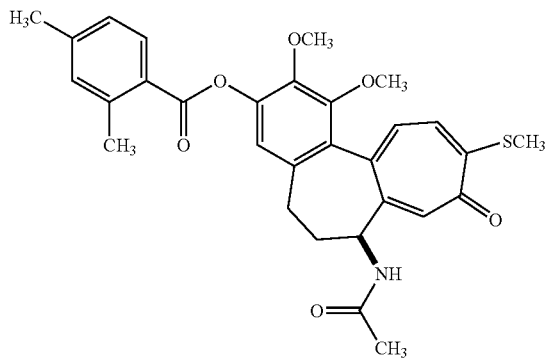 [SMILES: COc1c(OC(=O)c2ccc(C)cc2C)cc2c(c1OC)-c1ccc(SC)c(=O)cc1[C@@H](NC(C)=O)CC2]

3-[2,4-Dimethylbenzoyl]-3-demethylthiocolchicine can be prepared in a similar process as in Example 5 using 2,4-dimethylbenzoyl chloride (CAS No. 21900-42-5).

Example 7

3-[3-Oxobutanoate]-3-demethylthiocolchicine

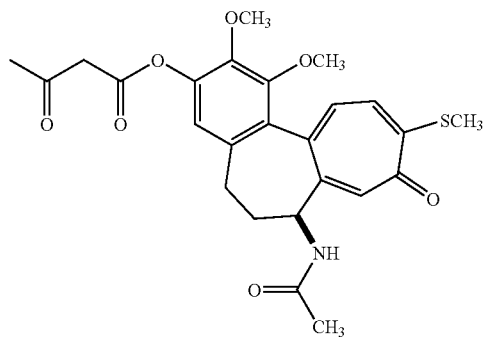 [SMILES: COc1c(OC(=O)CC(C)=O)cc2c(c1OC)-c1ccc(SC)c(=O)cc1[C@@H](NC(C)=O)CC2]

3-Demethylthiocolchicine (1 mmol) and 3-oxobutanoic acid (CAS No. 541-50-4, 1 mmol) is dissolved in acetonitrile (5 ml), optionally in the presence of 4-(N,N-dimethylamino) pyridine (DMAP, 0.15 equivalents). A solution of dicyclohexylcarbodiimide (1 mmol) in 1 ml acetonitrile is added to the reaction mixture and allowed to stir for 12 hours. The reaction mixture is filtered, stripped of acetonitrile and the resulting material purified by flash chromatography on silica to yield the product 3-[3-oxobutanoate]-3-demethylthiocolchicine.

Example 8

3-[4-Oxohexanoate]-3-demethylthiocolchicine

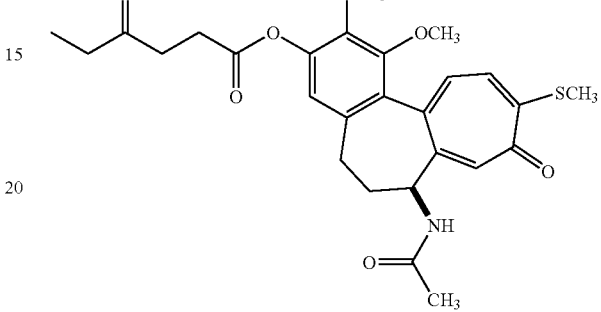

3-[4-oxohexanoate]-3-demethylthiocolchicine can be prepared in a similar process as in Example 7 using 4-oxohexanoic acid (CAS No. 1117-74-4).

Example 9

3-[3-(Dimethylamino)propanoate]-3-demethylthiocolchicine

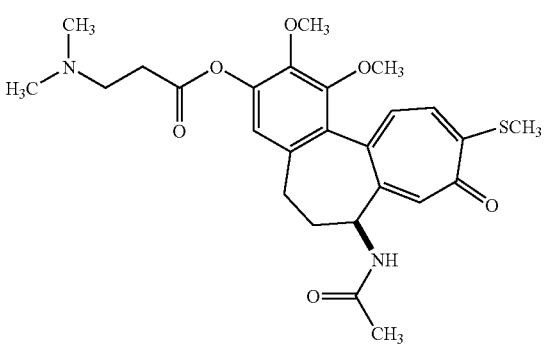 [SMILES: COc1c(OC(=O)CCN(C)C)cc2c(c1OC)-c1ccc(SC)c(=O)cc1[C@@H](NC(C)=O)CC2]

3-Demethylthiocolchicine (1 mmol) and 3-(dimethylamino)propanoic acid (1 mmol) is dissolved in acetonitrile (5 ml), optionally in the presence of 4-(N,N-dimethylamino) pyridine (DMAP, 0.15 equivalents). A solution of dicyclohexylcarbodiimide (1 mmol) in 1 ml acetonitrile is added to the reaction mixture and allowed to stir for 12 hours. The reaction mixture is filtered, stripped of acetonitrile and the resulting material purified by flash chromatography on silica to yield the product 3-[3-(dimethylamino)propanoate]-3-demethylthiocolchicine.

Example 10

3-[Isonicotinoyl]-3-demethylthiocolchicine

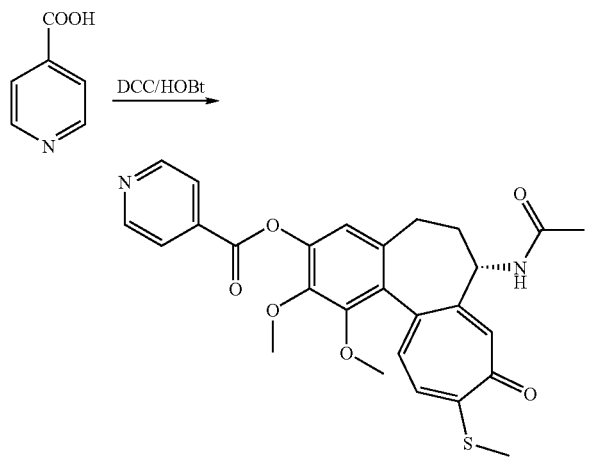

3-[Isonicotinoyl]-3-demethylthiocolchicine was prepared by charging 1.0 g (0.0083 mol) isonicotinic acid and 40.0 ml dichloromethane at room temperature in a 250 ml three neck round bottomed flask equipped with magnetic stirrer, nitrogen balloon and thermo probe. The reaction mixture was cooled to 0-5° C. Diisopropylethylamine (2.1 g, 0.01626 mol), N-hydroxybenzotriazole (HOBt, 1.138 g, 0.0097 mol), N,N'-dicyclohexylcarbodiimide (DCC, 2.18 g, 0.0105 mol), DMAP (0.9932 g, 0.00813 mol) and 3-demethylthiocolchicine (0.978 g, 0.00243 mol) was dissolved in 10.0 ml dimethylformamide (DMF) and added to the flask. The reaction mass was stirred at 0-5° C. for 30 minutes and then the temperature was raised to room temperature (RT) and stirred for 4-5 hr. The reaction mass was worked up by adding dichloromethane (30.0 ml) and 10% Hydrochloric acid solution (40.0 ml) to the reaction mass at RT. The organic layer was separated and washed with 10% hydrochloride solution (30.0 ml). The dichloromethane layer was washed with demineralized water twice (2×30 ml) and followed by brine solution. The resulting dichloromethane layer was dried over sodium sulfate. The organic layer was concentrated under high vacuum to get crude compound (0.7 g). The crude compound was dissolved in dichloromethane (DCM) and adsorbed on triethylamine (TEA) washed 100-200 mesh silica-gel. The crude compound was purified by column chromatograph using a column packed with TEA washed 100-200 mesh silica gel in hexane and distilled DCM. The column was eluted with 1%, 1.5%, and 2% methanol in DCM. The pure compound (0.3 g, yield: 23.8%) was confirmed $^1$H NMR and mass spectrometry.

Example 11

3-[Methyl acetate]-3-demethylthiocolchicine

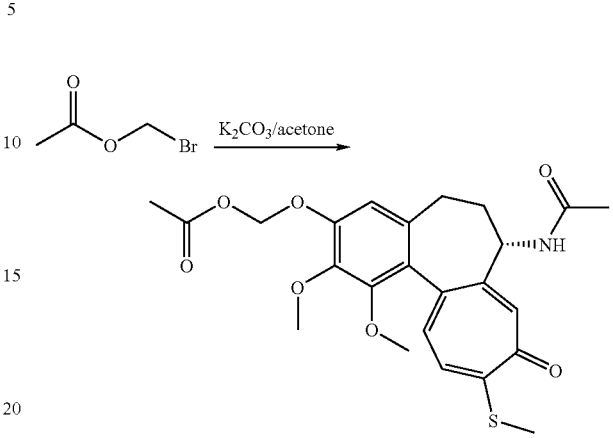

3-[Methyl acetate]-3-demethylthiocolchicine was prepared by charging 3-demethylthiocolchicine (0.5 g, 0.0012 mol), potassium carbonate (0.51 g, 0.0037 mol) and acetone (5.0 ml) at RT into a 50 ml 2-neck round bottom flask equipped with magnetic stirrer, reflux condenser, drying tube, and thermo probe. Bromomethyl acetate (0.286 g, 0.0018 mol) in acetone was added slowly to the reaction mass at RT. The reaction temperature was slowly raised to 60-65° C. and refluxed for 2-3 h. The reaction mass was cooled to RT, and acetone was distilled completely under vacuum at 40-45° C. The reaction mass was quenched with water and extracted into ethyl acetate (2×15 ml). The organic layer was washed with water followed by brine and dried over sodium sulphate. The organic layer was concentrated under vacuum at 45-50° C. to obtain a yellow crude material that was co-distilled with heptane to get free solid (0.6 g). The crude compound was dissolved in DCM and adsorbed on TEA washed 100-200 mesh silica-gel. The crude material was chromatographed on a column packed with TEA washed 100-200 mesh silica gel in hexane and distilled DCM. The column was eluted with 1%, 1.5%, 2% methanol in DCM. The compound fractions were distilled under vacuum at 40-45° C. then co-distilled with heptanes. The obtained compound was subjected to high vacuum for 2 h at RT to yield 0.25 g of pure product (yield: 59.4%). The compound was confirmed by $^1$H NMR, mass spectrometry, and HPLC.

Example 12

3-[2-Amino-3-(4-hydroxyphenyl)propanoyl]-3-demethylthiocolchicine

Stage-1:

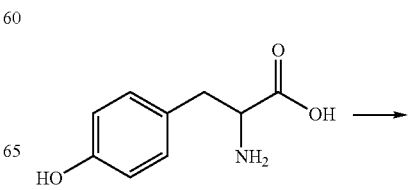

Stage-2:

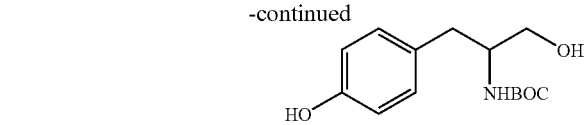

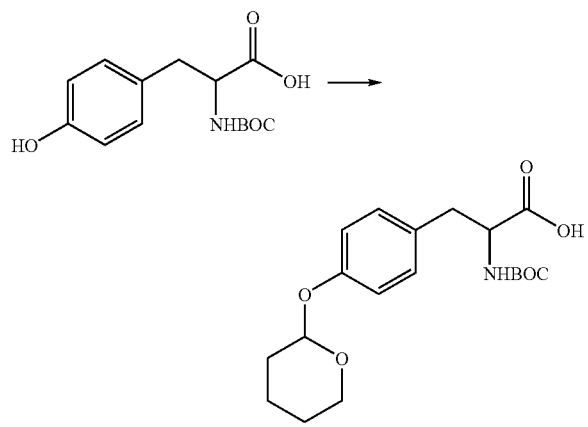

Stage-3:

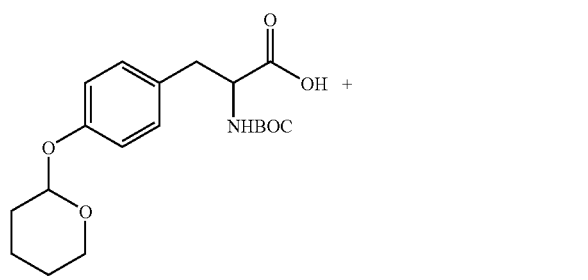

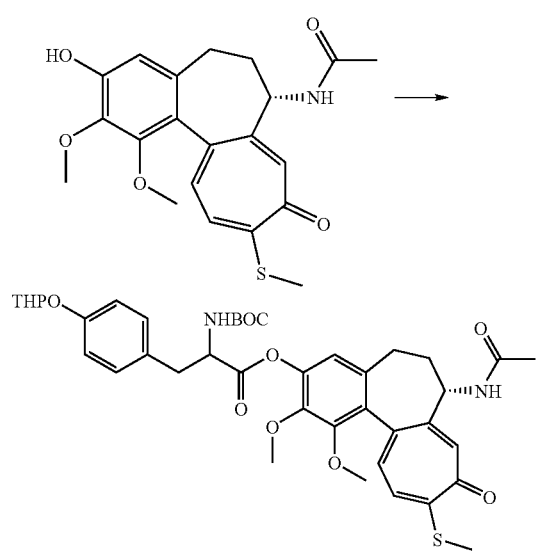

Stage-4:

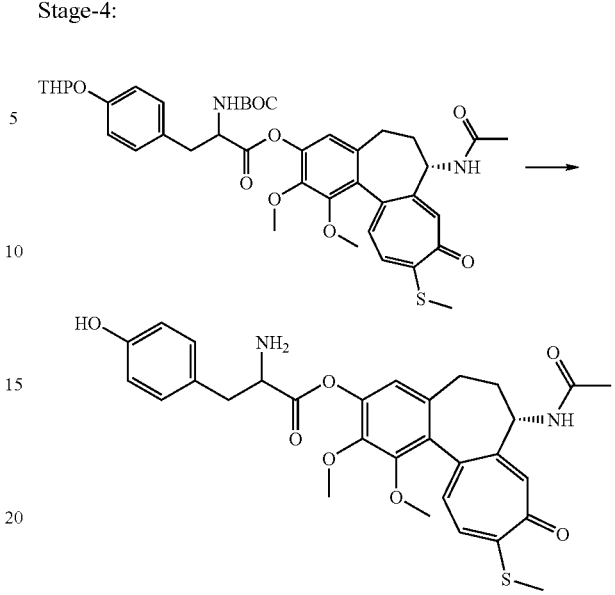

3-[2-Amino-3-(4-hydroxyphenyl)propanoyl]-3-demethylthiocolchicine was prepared by first tert-butyloxycarbonyl (BOC) protecting L-tyrosine in Stage-1. L-Tyrosine (10.0 g, 0.0552 mol) and 4M sodium hydroxide solution (40.0 ml) were charged at RT in a 500 ml three neck round bottomed flask equipped with mechanical stirrer, addition funnel, guard tube, thermo probe and reflux condenser. BOC-anhydride (24.0 g, 0.110 mol) dissolved in 30.0 ml acetone was added slowly drop wise to the flask at RT. The reaction mass temperature was raised to 50-55° C. and maintained at this temperature for 6-7 h. The reaction mass was dissolved in demineralized water (250.0 ml 25 w/v) and cooled to 0-5° C. The pH of the reaction mass was adjusted to 2-3 by adding 1M potassium hydrogen sulfate and the aqueous layer was extracted with ethyl acetate. The organic layers were washed with demineralized water followed by brine. The resulting organic layer was dried over sodium sulphate and concentrated to 15 g of white solid (96.7% yield).

In Stage-2 the phenol of the BOC protected L-tyrosine was protected by forming a tetrahydropyranyl (THP) ether. BOC protected L-tyrosine (3.1 g, 0.011 mol) and 31.0 ml DCM at RT were charged to a 100 ml two neck round bottomed flask equipped with magnetic stirrer, guard tube, and addition funnel. The reaction mass was cooled to 0-5° C. and pyridinium tosylate (0.27 g, 0.0011) and 3,4-dihydropyran (1.39 g, 0.0165) in DCM was added to the reaction mass. The reaction was stirred at 0-5° C. for 15 minutes and temperature was raised to RT and stirred for 10-12 h. The reaction mass was then distilled under high vacuum and the residue was dissolved in ethyl acetate. The organic layer was washed with demineralized water, followed by brine. The resulting organic layer was dried over sodium sulphate and concentrated to a gummy syrup (weight of crude compound: 4.25 g).

The BOC-THP protected L-tyrosine was reacted with 3-demethylthiocolchicine in Stage-3. BOC-THP protected L-tyrosine (4.25 g, 0.0116 mol) and 170.0 ml DCM at RT were charged to a 250 ml three-neck round bottomed flask equipped with magnetic stirrer, nitrogen balloon, and thermo probe. The reaction mass was cooled to 0-5° C. and then diisopropylethylamine (3.0 g, 0.023 mol), HOBt (1.88 g, 0.0139 mol), DCC (3.12 g, 0.015 mol), DMAP (0.17 g, 0.0058 mol) 3-demethylthiocolchicine (4.65 g, 0.0116 mol) in 25.0 ml N,N-dimethylformamide were charged to the flask. The reaction mass was stirred at 0-5° C. for 30 minutes and further stirred at RT for 10-12 h. DCM (150.0 ml) and 10% cold sodium hydroxide solution (150.0 ml) were added to reaction mass at RT and stirred for 5 minutes. The organic layer was separated and washed with 10% cold sodium hydroxide solution (2×150 ml) and followed by demineralized water and brine. The organic layer was dried over sodium sulphate and concentrated to get crude compound (5.0 g). The crude compound was dissolved in DCM and adsorbed on TEA washed 100-200 mesh silica-gel. The crude compound was purified via column chromatography using a column packed with TEA washed 100-200 mesh silica gel in hexane and distilled DCM. The column was eluted with 1% methanol in DCM. Compound fractions were distilled under vacuum at 40-45° C. and the pure compound was confirmed by $^1$H NMR and mass spectrometry (Product weight 0.850 g).

Stage-4 Deprotection. The product from Stage-3 (0.5 g, 0.000874 mol) and 5.0 ml DCM were charged at RT to a 250 ml three neck round bottomed flask equipped with magnetic stirrer, nitrogen balloon, thermo probe and addition funnel. The reaction mass was cooled to −5 to 0° C. and methanolic.HCl was slowly drop wise to the reaction mass. The reaction was allowed to stir at RT for 10-12 hr. The reaction mass was distilled under vacuum below 40° C. to get crude product (0.4 g).

Example 13

3-[2-aminopropanoyl]-3-demethylthiocolchicine

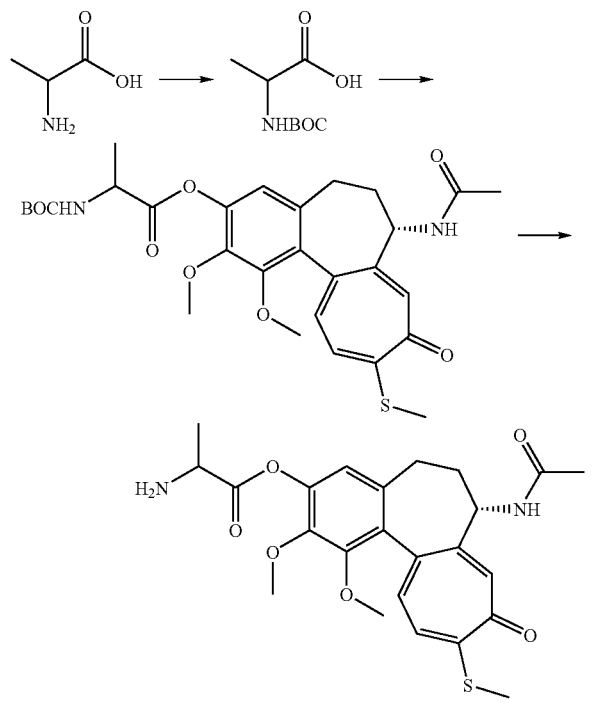

3-[2-Aminopropanoyl]-3-demethylthiocolchicine was prepared by first BOC protecting L-alanine L-Alanine (4.0 g, 0.0448 mol) and 16.0 ml 4M sodium hydroxide solution at RT were charged to a 100 ml three neck round bottomed flask equipped with magnetic stirrer, addition funnel, guard tube, thermo probe, and reflux condenser. BOC-anhydride (9.6 g, 0.0448 mol) in 20.0 ml acetone was added to the reaction mass slowly drop wise at RT. The reaction mass was heated to 50-55° C. and the reaction mass was maintained at this temperature for 4-5 h. Demineralized water (40.0 ml, 10 w/v) was add to reaction mass at 0-5° C. and the pH of the reaction mass was adjusted to 2-3 by adding 1M potassium hydrogen sulphate. The reaction mass was extracted with ethyl acetate and the organic layer was washed with water followed by brine. The resulting organic layer was dried over sodium sulphate and concentrated to a white solid (6.5 g).

The BOC protected L-alanine (3.0 g, 0.015 mol) and 30.0 ml DCM were charged at RT in a 250 ml three neck round bottomed flask equipped with magnetic stirrer and thermo probe. The reaction mass was cooled to 0-5° C. and diisopropylethylamine (4.1 g, 0.0317 mol), HOBt (2.57 g, 0.019 mol), DCC (4.25 g, 0.020 mol), DMAP (1.93 g, 0.015 mol) and 3-demethylthiocolchicine (3.18 g, 0.0079 mol) in 30.0 ml N,N-dimethylformamide was charged to the reaction flask. The reaction mass was stirred at 0-5° C. for 30 minutes and further stirred at RT for 6-7 h. DCM (150.0 ml) and 10% cold sodium hydroxide solution (150.0 ml) was added to reaction mass at RT and stirred for 5 minutes. The organic layer was separated and washed with 10% cold sodium hydroxide solution (2×150 ml), followed by demineralized water and brine. The resulting organic layer was dried over sodium sulphate and concentrated to get crude compound (4.3 g). The product was confirmed by $^1$H NMR.

The BOC-protected product was deprotected to 3-[2-aminopropanoyl]-3-demethylthiocolchicine using methanolic.HCl. BOC-coupled-alanine (0.5 g, 0.000874 mol) and 5.0 ml DCM at RT were charged to a 250 ml three neck round bottomed flask equipped with magnetic stirrer, nitrogen balloon, thermo probe and addition funnel. The reaction mass was cooled to −5° to 0° C. and 5.0 ml of methanolic.HCl was slowly added drop wise to reaction mass and allowed to stir for 30 minutes, and then stirred at RT for 10-12 h. The reaction mass was distilled under vacuum below 40° C. to get crude product (0.5 g) which contained 3-demethylthiocolchicine along with desired compound. The product was confirmed by mass spectrometry.

Example 14

3-[2-(Dimethylamino)acetyl]-3-demethylthiocolchicine

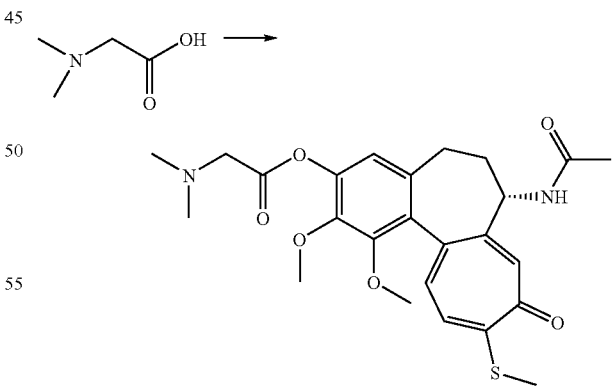

3-[2-(Dimethylamino)acetyl]-3-demethylthiocolchicine was prepared by charging 3-demethylthiocolchicine (0.5 g, 0.00124 mol) and dimethyl glycine (2-(dimethylamino)acetic acid, 0.51 g, 0.00498 mol) in 15.0 ml DCM at RT into a 50 ml two neck round bottom flask equipped with magnetic stirrer, nitrogen balloon, and thermo probe. The reaction mass was cooled to 10° C. and diisopropyl ethylamine (1.13 g, 0.0087 mol), 2-(7-aza-1H-benzotriazole-1-yl)-1,1,3,3-tetramethyluronium hexafluorophosphate (HATU, 0.947 g, 0.00249 mol) and DCM was added at same temperature and stirred for 5 min at same temperature. The reaction mass temperature was raised to RT and stirred for 1-1.5 h. DCM was distilled completely from the reaction mass under vacuum at 30-35° C. The crude gummy material was subjected to high vacuum at RT for 2-3 h to yield 2.1 g crude compound having a mass matching the expected compound (m/z (M+1)=487.

Example 15

3-[2-sulfoacetyl]-3-demethylthiocolchicine

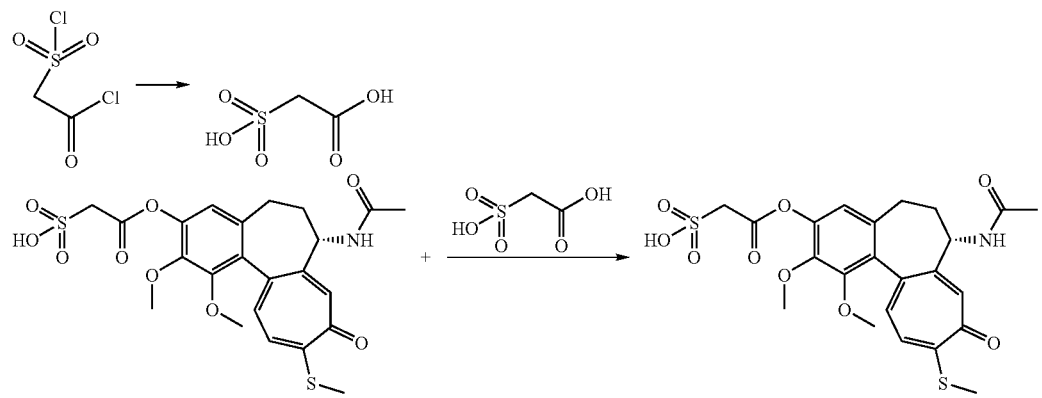

2-Sulfoacetic acid was prepared by charging chlorosulfonyl acetyl chloride (0.5 g, 0.0028 mol) in a 50 ml round bottomed flask equipped with magnetic stirrer. The reaction mass was cooled to 0-5° C. and ice cold water was added slowly at 0-5° C. The reaction mass was stirred at RT for 5 h. Water was completely distilled from the reaction mass at 45-50° C. under high vacuum to yield 0.54 g 2-sulfoacetic acid.

The 2-sulfoacetic acid (0.2 g, 0.0014 mol) and DCM (20 ml) were charged to a 50 ml two neck round bottomed flask equipped with magnetic stirrer, nitrogen inlet and thermo probe. The reaction mass was cooled to 0-5° C. and diisopropyl ethyl amine (0.8 g, 0.0062 mol) was slowly to the reaction mass at 0-5° C., followed by HATU (0.94 g, 0.0024 mol) at 0-5° C. followed by stirring for 5-10 min. 3-Demethylthiocolchicine (0.5 g, 0.0012 mol) was added at 0-5° C. and the reaction mass was stirred at RT for 1 h. DCM was completely distilled from the reaction mass and the crude product was purified by column chromatography using silica gel (100-200 mesh). The obtained compound contained 3-demethylthio colchicine along with desired compound.

Example 16

Determination of Muscle Relaxant Activity, Method A or B

Method A

Muscle relaxant activity is evaluated by recording the polysynaptic reflex in normal rats. Male Sprague-Dawley rats (200-500 g) are treated with intraperitoneal doses of thiocolchicine derivative in distilled water with a drop of 0.05% Tween-80 at doses of 3, 10, and 30 mg/kg. The flexor reflex is elicited by electric shocks to the sural nerve innervation area in the right hindpaw of the rats via stainless steel needles inserted subcutaneously. The flexor reflex is recorded as electromyogram activity via needle electrodes inserted in the ipsilateral posterior biceps femoris/semitendinosus muscles. The stimulus parameters are 0.2-0.5 ms and 0.2 Hz and activates mainly Aδ fibers. The stimulus intensity is defined by the recording conditions within each experiment such that the stimulus is sufficient to produce a stable response (8-12 mA). The electromyogram is amplified, filtered (10-1000 Hz), rectified and integrated within a time-window from 8-10 until 35-40 ms after the stimulus. The magnitude of these reflexes after drug administration is expressed as a percentage of the mean value of the predrug control period. A two-way ANOVA and Dunnett's test are performed. Thiocolchicoside is used as the reference compound.

Method B

Muscle relaxant activity is evaluated with the rota-rod test. Swiss male mice weighing 20-25 g are treated intraperitoneally with a thiocolchicine derivative at doses of 1, 3, and 10 mg/kg, thirty minutes before the test. Relaxant activity on striated muscles is evaluated by testing the resistance of the mice to the stimuli of a rotating plane revolving at increasing rate, from 2 to 50 r.p.m. Thiocolchicoside is used as the reference compound.

Example 17

Orally Disintegrating Tablet

A spray-dried mixture (550 grams) of mannitol and sorbitol in an 80:20 ratio (SPI Pharma Inc.), 61.00 grams of crospovidone and 1.5 grams of colloidal silicon dioxide are blended. The thiocolchicine derivative of Example 1 (400 grams) is then blended with the excipient mixture, optionally with flavor, color, high intensity sweetener, and food acid. Finally, magnesium stearate or sodium stearyl fumarate (16 grams) is added and blended. The final mixture is tableted using standard tableting procedures. The final mixture can be compressed into tablets using low force (4-20 kN) to form the orally disintegrating tablets. The orally disintegrating tablet dissolves in the oral cavity in less than seven minutes.

Orally disintegrating tablet containing the thiocolchicine derivatives of Examples 2 to 15 can be prepared in similar fashion.

Example 18

Orally Dissolving Strip

An orally dissolving strip is prepared by dissolving polyethylene oxide in water followed by the addition of polyethylene glycol (plasticizer), a sweetening agent (acesulfame potassium), sodium citrate, and polyoxyl castor oil. The thiocolchicine derivative of Example 1 is then added and mixed before casting a film on a Teflon surface using a BYK-Gardner film casting knife. The film is dried in an oven at a temperature of about 50-80° C. until dried. The dried film is then cut to size. The orally dissolving strip dissolves in the oral cavity in less than 60 seconds.

Orally dissolving strips containing the thiocolchicine derivatives of Examples 2 to 15 can be prepared in similar fashion.

The terms "comprising", "having", "including", and "containing" are to be construed as open-ended terms (i.e., meaning "including, but not limited to"). The terms "a" and "an" do not denote a limitation of quantity, but rather denote the presence of at least one of the referenced item. The term "or" means "and/or". The endpoints of all ranges directed to the same component or property are inclusive and independently combinable.

Unless defined otherwise, technical and scientific terms used herein have the same meaning as is commonly understood by one of skill in the art to which this invention belongs.

Embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound according to structure (I)

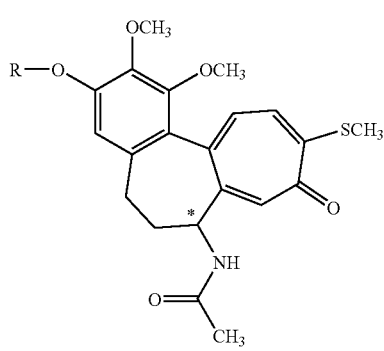

(I)

wherein R is b.) an amino acid derivative linked through the carboxylate group selected from the group consisting of alanine and tyrosine;

c.) —$CH_2$—O(C=O)$R^2$ where $R^2$ is methyl, ethyl, n-propyl, isopropyl and * is in the S configuration;

d.) —C(=O)$R^3$, where $R^3$ is pyridyl and * is in the S configuration; or f.) —C(=O)$(CH_2)_xSO_3R^4$ where $R^4$ is hydrogen or $C_1$-$C_3$ alkyl, x is 1 or 2 and * is in the S configuration;

or a pharmaceutically acceptable salt, crystalline form, non-crystalline form, or stereoisomer thereof.

2. The compound of claim 1, wherein R is b.) an amino acid derivative linked through the carboxylate group selected from the group consisting of alanine and tyrosine, or a pharmaceutically acceptable salt, crystalline form, or non-crystalline form thereof.

3. The compound of claim 1, comprising the S isomer, wherein R is c.) —$CH_2$—O(C=O)$R^2$ where $R^2$ is methyl, ethyl, n-propyl, or isopropyl, or a pharmaceutically acceptable salt, crystalline form, or non-crystalline form thereof.

4. The compound of claim 1, comprising the S isomer, wherein R is d.) —C(=O)$R^3$, where $R^3$ is pyridyl, or a pharmaceutically acceptable salt, crystalline form, or non-crystalline form thereof.

5. The compound of claim 1, comprising the S isomer, wherein R is f.) —C(=O)$(CH_2)_xSO_3R^4$ where $R^4$ is hydrogen or $C_1$-$C_3$ alkyl and x is 1 or 2, or a pharmaceutically acceptable salt, crystalline form, or non-crystalline form thereof.

6. The compound of claim 1, wherein the compound is

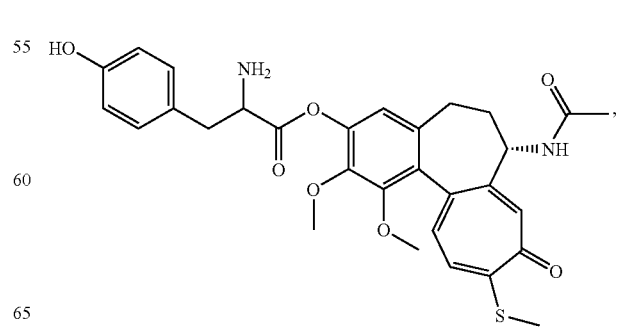

27
-continued
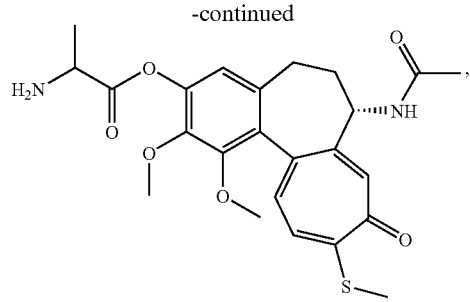
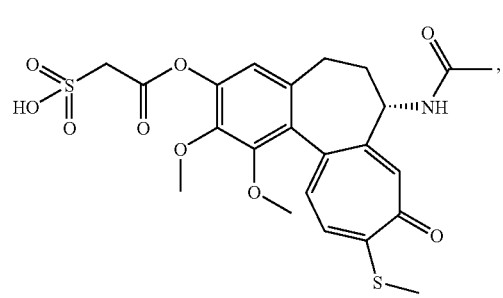
28
-continued
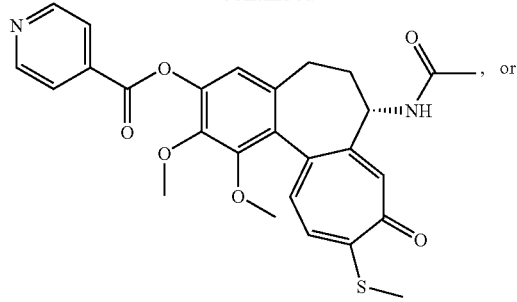
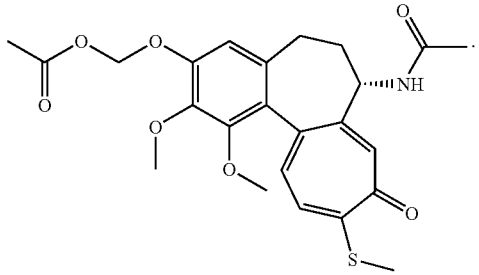
* * * * *